United States Patent [19]
Brown

[11] 3,937,216
[45] Feb. 10, 1976

[54] PNEUMATIC TRACTION MEANS FOR MEDICAL PATIENTS

[75] Inventor: Edmund J. Brown, Topanga, Calif.

[73] Assignee: Pneumatic Traction Company, Van Nuys, Calif.

[22] Filed: Sept. 9, 1974

[21] Appl. No.: 504,182

[52] U.S. Cl. ................................ 128/75; 128/84 C
[51] Int. Cl.[2] .......................................... A61H 1/02
[58] Field of Search ................... 128/75, 84, 70, 71

[56] References Cited
UNITED STATES PATENTS

| | | | |
|---|---|---|---|
| 3,343,532 | 9/1967 | Zumaglini | 128/75 |
| 3,667,457 | 6/1972 | Zumaglini | 128/75 |
| 3,716,049 | 2/1973 | Kaplan | 128/75 |
| 3,847,146 | 11/1974 | Cushman | 128/75 |

FOREIGN PATENTS OR APPLICATIONS

| | | | |
|---|---|---|---|
| 1,024,205 | 2/1958 | Germany | 128/75 |

Primary Examiner—Robert W. Michell
Assistant Examiner—J. Yasko
Attorney, Agent, or Firm—Lyon & Lyon

[57] ABSTRACT

A means for applying traction to a medical patient which includes a pneumatic cylinder and piston and a means for pressurizing the cylinder so as to apply a predetermined traction force. One embodiment further includes a storage cylinder to minimize change in traction force with change in position of the piston and a hand operated pumping cylinder and piston mounted in the storage cylinder. Another embodiment utilizes an extraneous source of pneumatic pressure, pressure regulating valve and a hand operated relief valve to permit cyclic application of traction.

7 Claims, 6 Drawing Figures

PNEUMATIC TRACTION MEANS FOR MEDICAL PATIENTS

BACKGROUND OF THE INVENTION

Traction devices for use by doctor's patients involve a framework secured to the bed, various devices for attachment to the patient depending on the nature of the injury requiring traction, tension lines extended through pulleys to the head or foot of the bed, and weight units attached to the ends of the tension lines. The number of weight units is increased or decreased to adjust the tension load.

SUMMARY OF THE INVENTION

The present invention is directed to a pneumatic means for applying tension to the bodies of medical patients which eliminates the need for weights as well as minimizing the need for tension lines, and is summarized in the following objects:

First, to provide a traction means which utilizes a pneumatic cylinder and piston unit, one end arranged for attachment to the framework provided on a hospital bed for traction purposes, the opposite end arranged for attachment to the various straps, brands and splints or the like applied by the physician or attendant to the patient.

Second to provide a traction means, as indicated in the previous object, wherein a storage cylinder or reservoir is provided to minimize change in the traction force with change in position of the piston.

Third to provide a traction means, as indicated in the preceeding objects, in which an embodiment thereof includes a manually operated pump cylinder and piston contained in the reservoir in covenant relation to the traction unit; and further includes a readily accessible means for relieving the traction force.

Fourth, to provide a traction means for patients wherein air is supplied from an extraneous source and a hand held manually controlled valve means is provided which is adjustable as to the traction force applied and is readily operated so that the traction force may be applied intermittently.

Figure 1:
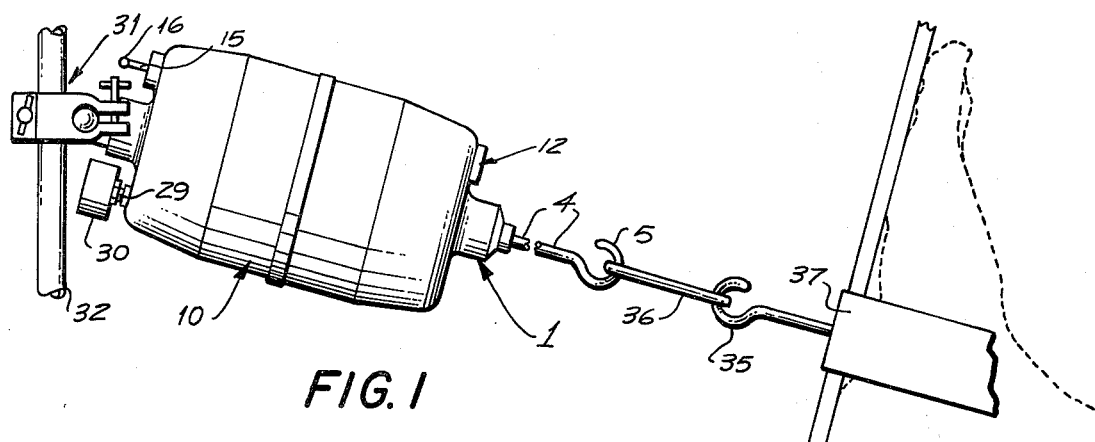
FIG. 1 is a side view of the pneumatic traction means showing fragmentarily the frame to which it is attached and indicating by broken lines the outline of a patient's foot sole plate and harness as it would appear if the foot and leg of a patient were under traction.

The pneumatic traction means includes a traction unit 1 having a cylinder 2 and a piston 3 connected to a stem 4. The extremity of the stem 4 is provided with a hook end 5.

The cylinder 2 receives an end fitting 6 having a vent opening 7 and a mounting stem 8. The opposite end of the cylinder 2 is provided with a second end fitting 9 having an opening provided with a seal ring, not shown through which the piston stem 4 extends. Also the end fitting 9 is sealed with respect to the cylinder.

The cylinder 2 is encased in a reservoir shell 10 substantially larger in volume than the cylinder. The shell includes end walls 11 through the extremities of the cylinder 2 extends in field relation to the end walls.

Mounted within the reservoir shell 10 at one side of the traction unit 1 is a pump unit 12 which includes a cylinder 13, and a piston 14 having a stem 15. The outer end of the stem 15 is provided with a handle 16. The stem extends through an end fitting 17 provided in the cylinder 13 which fitting is provided with a vent opening 18.

Figure 3:
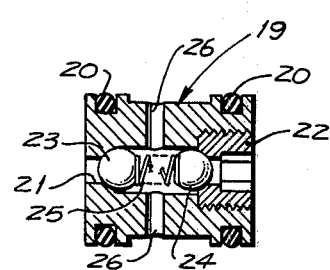
FIG. 3 is an enlarged sectional view taken through 3—3 of FIG. 2 showing a manually releasable valve means.

The cylinder 13 receives a valve fitting 19, shown best in FIG. 3 in the form of a cylindrical member having end seals 20 and a central bore 21. One end of the bore 21 receives a tubular set screw 22 which is sealed in place. Within the bore 21, is a pair of opposed check valves 23 and 24 forced against valve seats by an interposed spring 25.

The central bore 21 is intersected by one or more outlet passages 26 which communicate with the interior of the reservoir shell 10 through outlet ports 27 provided in the surrounding portion of the cylinder 13. The cylinder 2 is also provided with ports 28 communicating with the interior of the reservoir shell 10.

Provided in one of the end walls of the reservoir shell, or otherwise located is a fitting 29 screwthreaded to receive the stem of a pressure gage 30.

Figure 2:
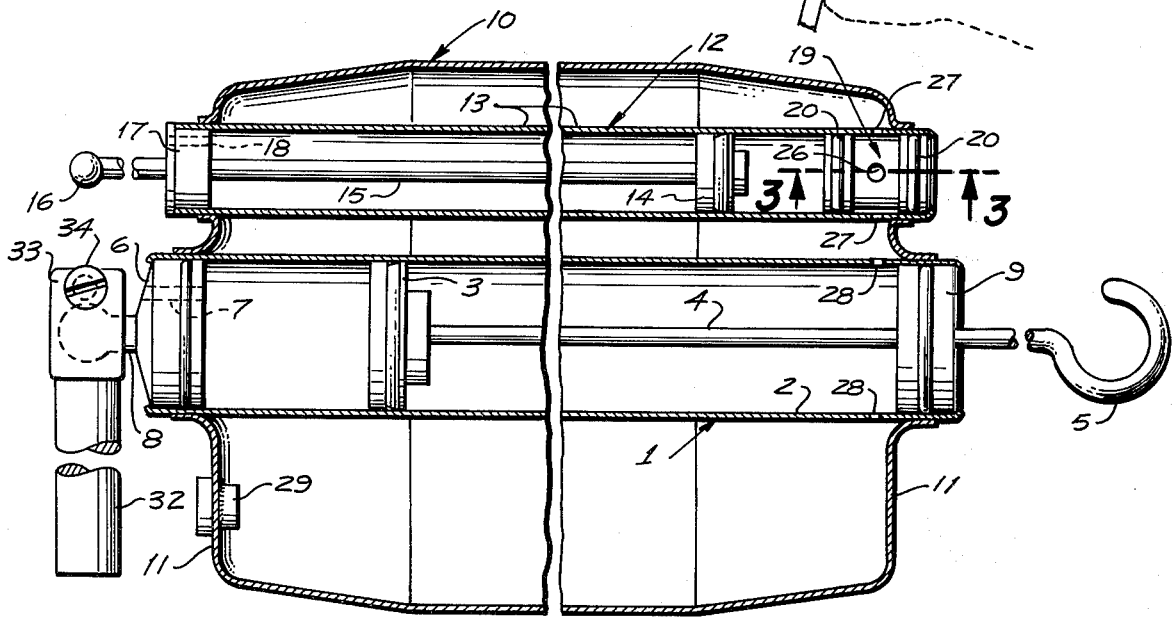
FIG. 2 is a longitudinal sectional view of the pneumatic traction means.

Operation of the traction means shown in FIGS. 1 through 3 is as follows:

The traction means is adapted to be attached to conventional framework 31 indicated fragmentarily in FIG. 1, which is attached to a patient's bed. Such frame work is normally used in conjunction with a set of weights and tension lines or cables passing over pulleys and connected to the various harnesses and fittings attached to the patient to be treated.

The traction means is intended to be attached to such frame work in place of the weight members and the connecting tension lines. For this purpose there is provided a mounting bar 32. The stem 8 is provided with a ball portion forming with the mounting bar a universal joint 33. The universal joint 33 may be provided with a screw fastener 34 or the like so that the universal joint may be secured in any adjusted position.

The hook end 5 on the stem 4 is connected in a conventional manner to, such as a loop 36, to a second hook 35 or other means forming part of a conventional harness or other equipment 37 applied by a doctor or attendant to the desired part of the patient's body. Upon pressurizing the traction unit by use of the hand pump 12 the pressure in the reservoir 10 and cylinder 2 may be adjusted so as to apply and maintain the desired traction force.

Whenever it is desired to release the traction force, a simple tool such as a ball point pen or pencil may be manually inserted in the valve fitting 19.

Figure 5:
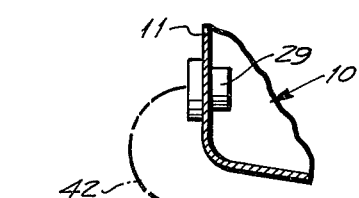
FIG. 5 is a sectional view thereof taken through 5—5 of FIG. 4.
Figures 4, 6:
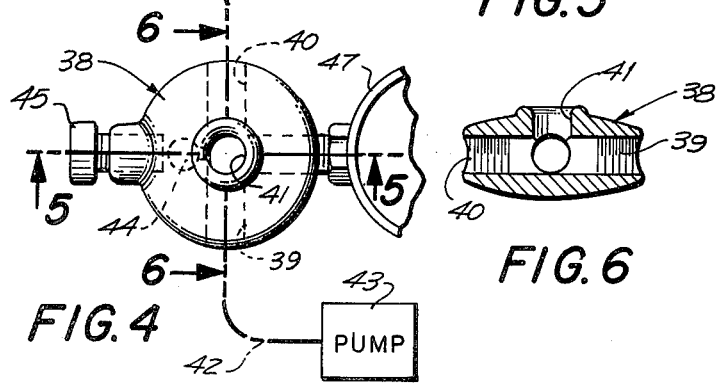
FIG. 4 is a side view of a manually operated control indicating diagrammatically its connection between a pump and the traction means.
FIG. 6 is a sectional view thereof taken through 6—6 of FIG. 4.

Reference is now directed to FIGS. 4, 5 and 6. It is sometimes desirable to apply the traction force intermittently. This may be accomplished by a manually operated valve unit 38 including a valve body having a transverse bore forming an inlet 39 and an outlet 40 intersected by a manually closable vent port 41. The valve body is interposed in a flexible flow line 42 extending between a pump 43 or other source of pneumatic pressure and the fitting 29. The valve unit is also provided with a relief valve 44 backed by a set screw 45 and spring 46. Also a gage 47 may be provided.

Operation of the embodiment shown in FIGS. 4, 5 and 6 is as follows:

The valve unit 38 is held by a nurse or attendant or by the patient, in such a manner that the vent port 41 may be readily closed by the user's finger or thumb. When closed, traction force is applied to the stem 4; when the vent port is opened the traction force is relieved. The amount of traction force is determined by the setting of the relief valve 44. The presence of the reservoir 10 insures a gradual application and relief of traction force; however, if desired the reservoir 10 may be omitted and the line connected directly to the cylinder 2 of the traction unit 1.

Having fully described my invention it is to be understood that I am not to be limited to the details herein set forth, but that my invention is of the full scope of the appended claims.

I claim:

1. A pneumatic means attachable to a mounting means fixed to a bed or other means supporting a patient for applying a traction force to the patient said traction applying means comprising:
   a. a traction unit including a cylinder, piston and stem extending through one end of the cylinder, the traction unit forming a pressure chamber between the piston and end of the cylinder through which the stem emerges;
   b. means for attaching the traction unit cylinder to said mounting means;
   c. means for attaching the stem to the patient;
   d. and means for pressurizing the pressure chamber to apply a traction force urging the stem inwardly to apply tension through the stem to the patient.

2. A traction means as defined in claim 1, which further comprises:
   a. a reservoir in communication with the traction cylinder and subject to the pressure therein to minimize change in pressure in the pressure chamber due to change in position of the piston resulting from change in position of the patient, thereby movement of the patient produces minimum change in the traction force.

3. A traction means as defined in claim 2, wherein:
   a. the reservoir surrounds the traction cylinder;
   b. and the pressurizing means is a manually operable pump mounted in the reservoir and accessible from the exterior thereof.

4. A traction means as defined in claim 1, wherein:
   a. a low capacity check valve normally retains the pressure in the traction cylinder and is manually accessible to bleed air from the traction cylinder to effect gradual releive the traction force.

5. A traction means as defined in claim 1, wherein:
   a. the pressurizing means includes a source of fluid pressure, a pressure line between the fluid pressure source and the traction cylinder, and a manually closable vent port in the pressure line for relieving the traction force, the vent port adapted to be intermittently closed and opened to effect repeated application and relief of traction force.

6. A pneumatic means attachable to a mounting means and to a patient for applying a traction force to the patient, said traction applying means comprising:
   a. a traction unit including a cylinder, piston and stem;
   b. means for interposing the traction unit between the mounting means and a patient;
   c. a reservoir shell surrounding the traction unit cylinder and joined to the ends thereof; a pump unit including a cylinder, piston, stem and handle, the pump unit cylinder being mounted in the reservoir shell and the handle being exposed for manual operation;
   d. the pump unit cylinder and traction unit cylinder having ports in communication with the reservoir whereby operation of the pump unit pressurizes both the reservoir shell and traction unit cylinder for application of a traction force on the patient.

7. A traction applying means as defined in claim 6, wherein:
   a. a check valve is positioned for manual access for depressurizing the reservoir shell and traction unit cylinder thereby relieve the traction force.

* * * * *